United States Patent

Klaubert et al.

[11] 4,087,606
[45] May 2, 1978

[54] 2-CYANO-3- OR 4-(SUBSTITUTED AMINO)OXANILIC ACID DERIVATIVES

[75] Inventors: Dieter H. Klaubert, West Chester; John H. Sellstedt, Pottstown; Charles J. Guinosso, King of Prussia, all of Pa.

[73] Assignee: American Home Products Corporation, New York, N.Y.

[21] Appl. No.: 800,769

[22] Filed: May 26, 1977

Related U.S. Application Data

[60] Division of Ser. No. 710,481, Aug. 4, 1976, Pat. No. 4,054,591, which is a continuation-in-part of Ser. No. 620,626, Oct. 3, 1975, abandoned.

[51] Int. Cl.² .................................... C07D 295/14
[52] U.S. Cl. ........................... 544/163; 260/239 A; 260/239 E; 260/293.75; 260/326.41; 544/58; 544/393
[58] Field of Search .......... 260/239 A, 239 E, 293.75, 260/326.41, 268 PH; 544/58, 163

[56] References Cited

U.S. PATENT DOCUMENTS 4,017,538   4/1977   Hall et al. ........................ 260/326.41

OTHER PUBLICATIONS

Wright et al., "Chem. Abstracts", vol. 84, (1976), No. 99619c.

*Primary Examiner*—Henry R. Jiles
*Assistant Examiner*—R. W. Ramsuer
*Attorney, Agent, or Firm*—Richard K. Jackson

[57] ABSTRACT

The 2-cyano-3-or 4-(substituted amino) oxanilic acid derivatives of the formula:

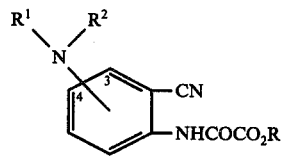

in which the group

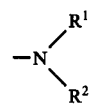

appears in the designated 3- or 4- position and

R is —H; an alkali metal; $^+NH_4$; alkyl of 1 to 6 carbon atoms, inclusive; aralkyl of 7 or 8 carbon atoms; or cycloalkyl of 5 or 6 carbon atoms;

$R^1$ is —H or alkyl of 1 to 9 carbon atoms;

$R^2$ is —H, alkyl of 1 to 9 carbon atoms or cycloalkyl of 3 to 6 carbon atoms;

$R^1$ and $R^2$, together, with the nitrogen atom to which they are attached, are aziridinyl, azetidinyl, pyrrolidinyl, piperidinyl, piperazinyl, 4-lower alkylpiperazinyl, morpholino or thiomorpholino;

and pharmaceutically acceptable acid addition salts thereof are anti-allergic agents.

6 Claims, No Drawings

2-CYANO-3- OR 4-(SUBSTITUTED AMINO)OXANILIC ACID DERIVATIVES

RELATED APPLICATIONS

This is a division of application Ser. No. 710,481 filed Aug. 4, 1976, now U.S. Pat. No. 4,054,591, and which is a continuation-in-part of Ser. No. 620,626, filed Oct. 3, 1975 now abandoned.

BACKGROUND OF THE INVENTION

Atopic allergic reactions are of the immediate hypersensitivity type as opposed to delayed hypersensitivity reactions, the latter being involved in such things as tuberculin sensitivity, transplant rejection, contact dermatitis and the like. Commonly recognized clinical conditions known to be at least in part due to atopic immediate hypersensitivity reactions, include seasonal and perennial allergic rhinitis (hay fever) and asthma, anaphylaxis, urticaria, conjunctivitis, angioaedema, eczema, various food and drug reactions and insect sting reactions. The substances most frequently responsible for atopic allergic reactions are plant pollen, animal feathers and danders, dust, milk and wheat, whether inhaled or injected. Atopic hypersensitivity is found in man, dog and other animals although its occurrence is exceptionally found in the lower animals.

Atopic (immediate hypersensitivity) reactions are characterized by the immunopathologic mechanism, the elements of which are: (1) a specific immunoglobulin (antibody; IgE in man, or homocytotropic antibody in the rat) is produced; (2) it is fixed to the surface of a target cell; (3) an antigen or allergin combines with the cell-bound antibody, which (4) induces release or one or more pharmacologic mediators, which in turn (5) induces symptoms of clinical disease such as increased vascular permeability, smooth muscle contraction, mucous gland hypersecretion, leukotaxis (especially eosinophilotaxis) and irritation of sensory nerve endings.

A compound which will interfere with the antigen-IgE reaction to prevent the release of mediators from the mast cell, or permit a non-productive antigen-antibody reaction without release of mediators, of necessity blocks the atopic allergic reaction thereby avoiding the resultant changes which are symptomatic of the disease.

The presence of antibodies associated with atopic reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigen in an individual sensitized by a variety of antigenic factors and is usually labile at about 56° C. after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin influences the cell membrane of a mast cell by reacting with an antigen, to initiate the reaction(s) within the mast cell which ultimately releases a mediator such as Bradykinin, SRS-A (slow reacting substance-A), histamine, and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histamines, anti-5-hydroxy-tryptamine (5-HT) or anti-inflammatories, or (4) stimulate and cell under attack to negate the action of the mediator through the action of bronchodilators such as Isoprel ® or a Xanthine.

The only commercial compound known to date to operate as an anti-allergic primarily by blocking reaction(s) within the mast cells, thereby preventing the production and release of mediators, is disodium cromoglycate (INTAL ®).

Disodium cromoglycate and compounds of that class are preventative in the sense that they must be administered to the sensitized animal prior to the allergic attack to be effective. They are not effective after the mediators have been released from the mast cells. Hence, their function is in preventing the release of mediators and/or a productive antibody-antigen reaction. As such, the rat PCA test (measuring the effect of mediator release) may be used to establish a compound as effective for all atopies because it establishes the diminished mediator release values in terms of the decrease in allergic response of the animal. The rat PCA test establishes the extent of mediator release from mast cells located in the rodent skin as a factor of the diminished effect on the skin of the test animal in relationship to the control animals.

The rat PCA (passive cutaneous anaphylaxis) test provides a classic procedure for evaluating the efficacy of drugs of the INTAL class relative to the response of the standard test animal resulting from antigen antibody interaction and mediator release. Extrapolation from an effect on the homocytotropic antibody of the rat to an effect on reaginic antibody (IgE) in the human is proper because of the well established relationship between these antibodies.

With knowledge of the mechanism of activity of INTAL in blocking the production of chemical mediators resulting from an antigen-antibody reaction and the variety of confirmed activities of INTAL in controlling or preventing immediate hypersensitivity reactions in man, as well as the close relationship between the rat homocytotropic antibody and IgE in the human, coupled with the fact that INTAL is the standard now used in the field for evaluating the efficacy of new anti-allergic compounds for atopic allergic reactions via the rat PCA test must lead to the practical conclusion that compounds which are active in the rat PCA test can, with very reasonable assurance, be projected as active anti-allergic agents in man, dog, etc.

As new anti-allergics are being developed, their activity mechanism is related to that of INTAL as the standard because of its known activity in man and its activity in the rat PCA test. In this regard see Pfister et al., J. Med. Chem., vol. 15, No. 10, pp. 1032–1035 (1972); Broughton et al., Nature, vol. 251, pp. 650–652, Oct. 18, 1971; and Assem et al., British Med. Journal, Apr. 13, 1974, pp. 93–95.

DESCRIPTION OF THE INVENTION

In accordance with this invention, there is provided a group of chemical compounds, useful for inhibiting development of the physical symptoms attending an atopic allergic reaction, presenting the formula:

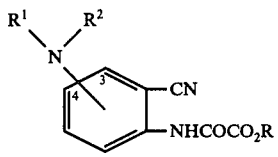

in which
R is —H; an alkali metal; $^+NH_4$; alkyl of 1 to 6 carbon atoms, inclusive; aralkyl of 7 or 8 carbon atoms; or cycloalkyl of 5 or 6 carbon atoms;
$R^1$ is —H or alkyl of 1 to 9 carbon atoms;
$R^2$ is —H, alkyl of 1 to 9 carbon atoms or cycloalkyl of 3 to 6 carbon atoms; and
$R^1$ and $R^2$, together with the nitrogen atom to which they are attached, are aziridinyl, azetidinyl, pyrrolidinyl, piperidinyl, piperazinyl, 4-lower alkyl-piperazinyl, morpholino or thiomorpholino;
and pharmaceutically acceptable acid addition salts thereof.

In the preceeding formula, the alkali metals contemplated for the group "R", are sodium, potassium or lithium. Embraced by the expression "alkyl of 1 to 6 carbon atoms" are such alkyl groups as methyl, ethyl, n-propyl, i-proyl, n-butyl, secondary butyl, tertiary butyl, pentyl and hexyl. The expression "aralkyl of 7 or 8 carbon atoms" is intended to embrace the benzyl and phenethyl radicals. The comtemplated cycloalkyl groups of 5 or 6 carbon atoms embrace cyclopentyl as well as cyclohexyl. The groups representing $R^1$ and $R^2$ may be normal or secondary alkyl containing from 1 to 9 carbon atoms each. Where $R^1$ and $R^2$ represent a cyclic group with the nitrogen atom depicted in the structural formula, they are represented as dimethylene, trimethylene, tetramethylene, pentamethylene, or the 3-oxa, aza, or thia-pentamethylene radicals (oxy, thio or imino di-ethylene). In those situations where $R^1$ and $R^2$ represent a heterocyclic group containing nitrogen, it is preferred to prepare the compounds in the form of their non-toxic pharmaceutically acceptable acid addition salts for the purpose of separation and recovery. Likewise, when $R^1$ and/or $R^2$ is hydrogen, that amino group is protected during reaction with the chloro oxalic acid ester followed ultimately by removal of the protecting group. For this purpose, any standard protecting group known to the art may be employed, the trimethylsilyl group being representative of the type of protecting group especially suitable for the purpose stated.

The expression, pharmaceutically acceptable acid addition salts, is used to include the non-toxic acid addition salts which may be formed with either organic or inorganic acids such as hydrochloric, hydrobromic, sulfuric, phosphoric, methane sulfonic, nitric, p-toluene sulfonic, acetic, citric, maleic, succinic acid and the like.

The preferred compounds from the standpoint of potency are those in which $R^1$ and $R^2$ are hydrogen or $R^1$ is lower alkyl and $R^2$ is hydrogen and the amino group

is in the 3-position.

The 3- or 4-substituted-2-cyanooxanilic acid compounds of this invention are generally produced by condensing an appropriately substituted 2-cyanoaniline with an activated oxalic acid half ester in which the substituent in 3- or 4-position is amino, alkylamino of 1 to 9 carbon atoms, dialkylamino of 1 to 9 carbon atoms in either alkyl moiety, cycloalkylamino of 5 to 6 carbon atoms, aziridinyl, azetidinyl, pyrrolidinyl, piperidinyl piperazinyl, 4-lower alkyl-piperazinyl, morpholino or thiomorpholino. By an activated oxalic acid half ester, Applicants embrace the acid halides, mixed anhydrides, azide, and the like groups employed in the production of amidic linkages.

The 2-cyano group may be formed optionally via dehydration of a correspondingly 2-carbamyl substituted precursor. Furthermore, a free amino group in 3- or 4-position may be produced by reduction of a nitro substituent after condensation with said activated oxalic acid half ester. The free amino group may be then mono- or dialkylated with groups which are optionally cyclizable. Likewise, the final product ester is saponified with an appropriate base to afford an alkali metal or ammonium salt.

The compounds of this invention have been demonstrated to relieve allergic manifestations when administered intraperitoneally and/or orally to sensitized rats.

The technique employed to establish the anti-allergic activity of the disclosed compounds is reported in Immunology, vol. 16, pp. (749–760 (1969) and involves four male Charles River rats (200–250 g. body weight) per group to provide a control, a host for administration of a standard anti-allergic compound (disodium cromoglycate) and animals for the test compound. The rats are injected intracutaneously or their shaved backs with sera from rats immunized with egg albumin and pertussis vaccine. Twenty-four hours after the initial injections, the test compound is administered intraperitoneally or orally at a maximum dosage level of 200 milligrams per kilogram host body weight. Five minutes later 1 milliliter of a 0.5 percent solution of Evans blue dye and 8 milligrams of egg albumin is injected intravenously. After 40 minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants have found that the compounds of this invention, in a manner believed to be similar to the function of INTAL, block reaction(s) in the mast cell leading to the production and release of mediators. The compounds of this invention permit the occurrence of a non-productive antigen-antibody interaction by effectively blocking the IgE type reaction. In sum, the compounds of this invention block the release of mediators commonly resulting from the antigen antibody reaction as exemplified in a passive cutaneous anaphylaxis test (PCA) using rat homocytotropic antibody—a known correlate of human reaginic antibody.

By analogy to disodium cromoglycate and its activity correlation between standard test animals, domestic animals and man, the compounds of this invention have been established as anti-allergic agents suitable for use as inhalants or by oral or parenteral administration.

Thus, the compounds of this invention are useful for suppressing allergic manifestations of atopic immediate sensitivity in warm-blooded human and non-human animals, the latter including domesticated animals such as the mouse, rat, hamster, gerbil, dog, cat, sheep, goat, horse, cow, and the like, by administering an effective amount of one or more of the compounds disclosed in ths application by oral, topical, intraperitoneal, intramuscular or intravenous routes. The compounds of this invention may be administered in conjunction with known compounds effecting antihistaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions.

The effective dose range in test animals has been established to be from about 0.01 milligrams per kilogram to a dosage resulting in substantially 100 percent prevention of the allergic response at 200 milligrams per kilogram host body weight, or less.

As an inhalant, the dose is 2 milligrams or less, administered as needed prior to attack. Thus, the dosage contemplated for human oral or intraperitoneal use based upon the potency of the compound administered lies from about 1 milligram to 2 grams, preferably 5 milligrams to about 1.5 grams in unit dosage form to be administered when necessary and to the degree of the desired response, in single or plural doses under the guidance of a physician.

Regarding the dosage to be used in the treatment of a specific atopic allergic reaction, the subjective observations of the attending physician are determinative. The human dose, like the dose for the dog, depends upon the specific allergy being treated, the size, age, response pattern and severity of the known allergic attack in the specific patient. No unusual skill is involved in establishing the most desirable dose size and regimen for a specific patient because the loss or suppression of the symptom is apparent to both the patient and the physician. The effective amount of the anti-allergic compound administered must be empirically determined subjectively.

Illustrative of the compounds of this invention, which are orally active are 2-cyano-3-(dimethylamino)oxanilic acid ethyl ester, demonstrating oral activity equivalent to 54% inhibition at 5 milligrams per kilogram host body weight; 67% inhibition at 25 milligrams per kilogram host body weight and 73% inhibition at 100 milligrams per kilogram host body weight, as well as 2-cyano-3-(4-methyl-1-piperazinyl)oxanilic acid ethyl ester hydrochloride which effects a 77% inhibition upon oral administration of 25 milligrams per kilogram host body weight. Illustrative of the compounds of this invention possessing anti-allergic activity upon intraperitoneal administration is 2-cyano-3-(1-piperidinyl)oxanilic acid ethyl ester which affords 93% inhibition at 200 milligrams per kilogram host body weight; the two compounds mentioned in the preceding sentence presenting respectively, 93% inhibition at 200 milligrams per kilogram host body weight and 88% inhibition at 200 milligrams per kilogram host body weight. As noted supra, the preferred compounds as those in which the amino group appears in 3-position as the free amino group or lower alkylamino group. These compounds have been found to effect 100% inhibition with as low as 0.10 milligrams per kilogram dosage administered intravenously with the sodium salt of [2-cyano-3-(methylamino)phenylamino]oxoacetic acid.

EXAMPLE 1

[2-Cyano-3-(Dimethylamino)Phenylamino]Oxoacetic Acid Ethyl Ester

To a solution of 9.7 g. of 2,6-dinitrobenzonitrile and 6.1 g. of dimethylamine hydrochloride in 100 ml. of dimethylformamide is added 6 g. of potassium hydroxide in 20 ml. of water. The solution is stirred for 4 hours, poured into ice water and the product, 2-dimethylamino-6-nitrobenzonitrile, is filtered and dried, m.p. 112°–116° C.

Analysis for: $C_9H_9N_3O_2$—Calculated: C, 56.54; H, 4.75; N, 21.98. Found: C, 56.28; H, 4.77; N, 21.77.

To a suspension of 5.7 g. of 2-dimethylamino-6-nitrobenzonitrile in 20 ml. of methanol and 17 ml. of concentrated hydrochloric acid is added 5.3 g. of iron powder in portions. The mixture is stirred for ½ hour, diluted with 200 ml. of water and extracted with methylene chloride which is dried and evaporated in vacuo to yield crude 2-amino-6-dimethylaminobenzonitrile.

To a solution of 3.4 g. of crude 2-amino-6-dimethylaminobenzonitrile and 1.6 g. of pyradine in 50 ml. of methylene chloride at 0° is added dropwise 2.7 g. of ethyl oxalyl chloride in 25 ml. of methylene chloride. The solution is stirred at 0° C. for 3 hours, warmed to room temperature and water is added. The organic phase is separated, dried and evaporated to give a yellow solid which is recrystallized from benzene-hexane to yield 3.2 g. of the title compound, m.p. 124°–126° C.

Analysis for: $C_{13}H_{15}N_3O_3$—Calculated: C, 59.76; H, 5.79; H, 16.08. Found: C, 59.47; H, 5.47; N, 16.08.

EXAMPLE 2

[2-Cyano-3-(1-Piperidinyl)Phenylamino]Oxoacetic Acid Ethyl Ester

To a solution of 19.3 g. of 2,6-dinitrobenzonitrile in 300 ml. of dimethylformamide is added 25.5 g. of piperidine and the resulting solution is warmed to 85° C. and kept at that temperature until the reaction is complete. The reaction mixture is poured into water, the product, 2-nitro-6-(1-piperidinyl)benzonitrile, is filtered and dried, m.p. 119°–121° C.

Analysis for: $C_{12}H_{13}N_3O_2$—Calculated: C, 62.32; H, 5.67; N, 18.17 Found: C, 62.32; H, 5.82; N, 18.26.

The 2-nitro-6-(1-piperidinyl)benzonitrile prepared in the preceding paragraph is converted to 2-amino-6-(1-piperidinyl)benzonitrile by iron reduction following the procedure of Example 1.

The title compound is produced by reaction of 2-amino-6-(1-piperidinyl)benzonitrile with ethyl oxalyl chloride, m.p. 98°–100° C.

Analysis for: $C_{16}H_{19}N_3O_3$—Calculated: C, 63.77; H, 6.36; N, 13.94. Found: C, 63.76; H, 6.37; N, 13.76.

EXAMPLE 3

[2-Cyano-3-(4-Methyl-1-Piperazinyl)Phenylamino]Oxacetic Acid Ethyl Ester Hydrochloride Following the procedure presented in the first paragraph of Example 2, with the exception that N-methylpiperazine is substituted for piperidine, 2-(4-methyl-1-piperazinyl)-6-nitrobenzonitrile is prepared, m.p. 126°–129° C.

Analysis for: $C_{12}H_{14}N_4O_2$—Calculated: C, 58.52; H, 5.73; N, 22.75. Found: C, 58.65; H, 5.87; N, 22.78.

To a solution of 4.92 g. of 2-(4-methyl-1-piperazinyl)-6-nitrobenzonitrile in 11 ml. of concentrated hydrochloric acid is added 3.4 g. of iron powder. The mixture is stirred for 30 minutes, poured into ice water and the pH is adjusted to 12. Methylene chloride is added, the whole mixture is filtered through celite, the methylene chloride is separated, dried and evaporated to give solid, crude product, 2-amino-6-(4-methyl-1-piperazinyl)benzonitrile.

A mixture 3.96 g. of crude 2-(4-methyl-1-piperazinyl)-6-aminobenzonitrile, 2.74 g. of ethyl oxalyl chloride is stirred for 2 hours at room temperature, poured into 1.68 g. of sodium bicarbonate in 25 ml. of water and stirred for 5 minutes. The organic layer is separated, dried and evaporated. The residue is dissolved in diethyl ether-ethanol, saturated diethyl ether-hydrogen chloride is added and the product is allowed to crystallize to give the pure title compound, m.p. 204°–206° C. (dec.).

Analysis for: $C_{16}H_{20}N_4O_3 \cdot HCl$—Calculated: C, 54.56; H, 6.00; N, 15.88; Cl, 10.05. Found: C, 54.53; H, 6.31; N, 15.90; Cl, 10.08.

Following the general preparative procedures exemplified in the preceding examples, by varying the amine reactant ($HNR^1R^2$) employed in the displacement reaction with 2,6-dinitrobenzonitrile, reducing the remaining nitro substituent to afford the reactive amino group and finally coupling that product with an oxalyl chloride ester, there is afforded a family of 2-cyano-3- or 4-(substituted amino)oxanilic acid esters which may be directly saponified to afford a salt, or readily hydrolyzed under mild conditions to yield the corresponding oxanilic acids which are in turn readily converted to the corresponding salts upon reaction with a desired base.

Various amines, $HNR^1R^2$, employed in the synthesis of the anti-allergic compounds of this invention and the final products, employing ethyl oxalyl chloride in each instance as representative of the simply oxalyl ester reactants employed in the synthesis, are:

| | NHR¹R² | |
|---|---|---|
| R¹ | R² | Ethyl Ester of |
| 1. —H | —CH₃ | 2-cyano-3-(methylamino)oxanilic acid |
| 2. —CH₃ | —CH₃ | 2-cyano-3-(dimethylamino)oxanilic acid |
| 3. —CH₃ | —CH(CH₃)₂ | 2-cyano-3-(isopropylmethylamino)oxanilic acid |
| 4. —H | —CH₂CH₃ | 2-cyano-3-(ethylamino)oxanilic acid |
| 5. —CH₂CH₃ | —CH₂CH₂CH₂CH₃ | 2-cyano-3-(ethylbutylamino)oxanilic acid |
| 6. —H | —CHCH₂CH₃ (CH₃) | 2-cyano-3-(sec-butylamino)oxanilic acid |
| 7. —CH₂CH₂CH₂CH₃ | —CH₂CH₂CH₂CH₃ | 2-cyano-3-(dibutylamino)oxanilic acid |
| 8. —H | heptyl | 2-cyano-3-(heptylamino)oxanilic acid |
| 9. —H | hexyl | 2-cyano-3-(hexylamino)oxanilic acid |
| 10. —H | —CH₂CH(CH₃)CH₃ | 2-cyano-3-(isobutylamino)oxanilic acid |

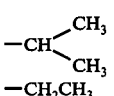

| NHR¹R² | Ethyl Ester of |
|---|---|
| 11. 1-pyrrolidinyl | 2-cyano-3-(1-pyrrolidinyl)oxanilic acid |
| 12. 1-piperidinyl | 2-cyano-3-(piperidino)oxanilic acid |
| 13. 4-methyl-1-piperazinyl | 2-cyano-(4-methyl-1-piperazinyl)oxanilic acid |

| NHR¹R² | Final Product Ethyl Ester of |
|---|---|
| 14. morpholino | 2-cyano-3-(morpholino)oxanilic acid |
| 15. thiomorpholino | 2-cyano-3-(thiomorpholino)oxanilic acid |
| 16. 1-azetidine | 2-cyano-3-(1-azetidinyl)oxanilic acid |
| 17. 1-aziridine | 2-cyano-3-(1-aziridinyl)oxanilic acid |

EXAMPLE 4

[2-Cyano-4-(Dimethylamino)Phenylamino]Oxoacetic Acid Ethyl Ester

To a solution of 4.6 g. of [2-(aminocarbonyl)-4-(dimethylamino)phenylamino]oxoacetic acid ethyl ester in 130 ml. of chloroform at 0° C. is added 2 ml. of phosphorus oxychloride and 13 ml. of triethylamine. The reaction is stirred at room temperature until complete (approximately 6 days). Water is added, the pH is adjusted to about 5 and the organic layer is separated, dried and evaporated. The product is recrystallized from ethanol, m.p. 150°–152° C.

Analysis for: $C_{13}H_{15}N_3O_3$—Calculated: C, 59.76; H, 5.79; N, 16.08. Found: C, 59.76; H, 6.02; N, 15.91.

[2-(Aminocarbonyl)-4-(dimethylamino)phenylamino]oxacetic acid ethyl ester is prepared by oxalation of 2-amino-5-dimethylaminobenzamide with ethyl oxalyl chloride as in Example 1, m.p. 203°–205° C.

Analysis for: $C_{13}H_{17}N_3O_4$—Calculated: C, 55.90; H, 6.14; N, 15.05. Found: C, 56.12; H, 6.23; N, 15.08.

2-Amino-5-dimethylaminobenzamide is obtained by treatment of 5-dimethylaminoisatoic anhydride hydrochloride with 1N ammonium hydroxide in a manner similar to the procedure of R. P. Staizer and E. C. Wagner, J. Org. Chem., 13, 347 (1948).

5-Dimethylaminoisatoic anhydride hydrochloride is obtained by treatment of the corresponding anthranilic acid with phosgene in a manner identical to that given in J. H. Sellstedt et al., J. Med. Chem., 18, 926 (1975) for 3,5-dimethyl anthranilic acid, m.p. 256°–258° C. (dec).

Analysis for: $C_{10}H_{10}N_2O_3 \cdot HCl$—Calculated: C, 49.49; H, 4.57; N, 11.55; Cl, 14.61. Found: C, 49.15; H, 4.54; N, 11.10; Cl, 14.57.

5-Dimethylaminoanthranilic acid is known, R. A. Rossi and H. E. Bertorello, An. Assoc. Quim. Argent., 55, 227 (1967).

EXAMPLE 5

[3-Amino-2-Cyanophenylamino]Oxoacetic Acid Ethyl Ester

The title compound is prepared by reduction of [3-nitro-2-cyanophenylamino]oxoacetic acid ethyl ester with 10% Pd. on charcoal and with cyclohexene in ethanol according to the procedure of I. D. Entwistle and R. A. W. Johnstone, J. Chem. Soc., Perkin I, 1300 (1975). The crude product is chromatographed on silica gel with chloroform and recrystallized from ethanol, m.p. 133°–136° C.

Analysis for: $C_{11}H_{11}N_3O_3$—Calculated: C, 56.64; H, 4.76; N, 18.02. Found: C, 56.58; H, 4.64; N, 18.20.

[3-Nitro-2-cyanophenylamino]oxoacetic acid ethyl ester is prepared by treatment of 2-amino-6-nitrobenzonitrile with ethyl oxalyl chloride as in Example 1, m.p. 111°–113° C.

Analysis for: $C_{11}H_9N_3O_5$—Calculated: C, 50.19; H, 3.45; N, 15.97. Found: C, 50.11; H, 3.44; N, 15.99.

2-Amino-6-nitrobenzonitrile is prepared as follows:

2,6-Dinitrobenzonitrile (19.3 g.) is dissolved in methanol (400 ml.) and dioxane (250 ml.) at reflux. To this is added conc. hydrochloric acid (60 ml.) followed by iron powder (18 g.) in portions. The mixture is left at reflux for 1 hr., and is evaporated to dryness. Water is added, the resultant solid is filtered off, dried and extracted with hot ethyl acetate. After filtration through Celite®, the product is allowed to crystallize, m.p. 196°–198° C.

Analysis for: $C_7H_5N_3O_2$—Calculated: C, 51.54; H, 3.09; N, 25.76. Found: C, 51.39; H, 3.01; N, 25.68.

EXAMPLE 6

[3-(Methylamino)-2-Cyanophenylamino]Oxoacetic Acid Ethyl Ester

Oxalation of 2-amino-6-methylaminobenzonitrile as in Example 1 gives the title compound, m.p. 137°–139° C.

Analysis for: $C_{12}H_{13}N_3O_3$—Calculated: C, 58.29; H, 5.30; N, 17.00. Found: C, 58.13; H, 5.32; N, 16.94.

2-Amino-6-methylaminobenzonitrile is prepared by iron reduction of 2-methylamino-6-nitrobenzonitrile as in Example 1.

2-Methylamino-6-nitrobenzonitrile is prepared as follows:

to 19.3 g. of 2,6-dinitrobenzonitrile in 150 ml. of dimethylformamide at 85° C. is added 25 ml. of 40% aqueous methylamine. The mixture is heated for 1 hour, poured into ice water and the product is removed by filtration, m.p. 203°–206° C.

Analysis for: $C_8H_7N_3O_2$—Calculated: C, 54.23; H, 3.99; N, 23.72. Found: C, 54.24; H, 3.70; N, 24.02.

EXAMPLE 7

[2-Cyano-3-(Ethylamino)phenylamino]Oxoacetic Acid Ethyl Ester

Crude 2-amino-6-ethylaminobenzonitrile is oxalated as in Example 1 to give the title compound, m.p. 99°–102° C.

Analysis for: $C_{13}H_{15}N_3O_3$—Calculated: C, 59.76; H, 4.79; N, 16.08. Found: C, 59.35; H, 5.89; N, 15.88.

Crude 2-amino-6-ethylaminobenzonitrile is prepared by iron reduction of 2-ethylamino-6-nitrobenzonitrile as in Example 1.

2-ethylamino-6-nitrobenzonitrile is obtained by displacement on 2,6-dinitrobenzonitrile with ethylamine as in Example 6, m.p. 114°–116° C.

Analysis for: $C_9H_9N_3O_2$—Calculated: C, 56.54; H, 4.75; N, 21.98. Found: C, 56.73; H, 4.75; N, 21.73.

EXAMPLE 8

[3-(Butylamino)-2-Cyanophenylamino]Oxoacetic Acid Ethyl Ester

This material is prepared following the procedure of Example 1, by oxalation of 2-amino-6-butylaminobenzonitrile, m.p. 101°–105° C.

Analysis for: $C_{15}H_{19}N_3O_3$—Calculated: C, 62.26; H, 6.62; N, 14.52. Found: C, 62.03; H, 6.42; N, 14.55.

2-amino-6-butylaminobenzonitrile is obtained by iron reduction as in Example 1.

2-butylamino-6-nitrobenzonitrile is obtained by the usual displacement reaction using butylamine, m.p. 72°–74° C.

Analysis for: $C_{11}H_{13}N_3O_3$—Calculated: C, 60.26; H, 5.98; N, 19.15. Found: C, 60.38; H, 6.09; N, 19.06.

EXAMPLE 9

[3-(Ethylmethylamino)-2-Cyanophenylamino]Oxoacetic Acid Ethyl Ester

Treatment of 2-amino-6-(ethylmethylamino)benzonitrile with oxalyl chloride as in Example 1 gives the product, m.p. 75°–78° C.

Analysis for: $C_{14}H_{17}N_3O_3$—Calculated: C, 61.08; H, 6.22; N, 15.26. Found: C, 60.77; H, 6.21; N, 15.34.

The amine is obtained by the usual iron reduction. 2-(ethylmethylamine)-6-nitrobenzonitrile is obtained by displacement with ethylmethylamine, m.p. 60°–63° C.

Analysis for: $C_{10}H_{11}N_3O_2$—Calculated: C, 58.53; H, 5.40; N, 20.48. Found: C, 58.84; H, 5.48; N, 20.81.

EXAMPLE 10

[2-Cyano-3-(Methylisopropylamino)Phenylamino]Oxoacetic Acid Ethyl Ester

The usual oxalation as in Example 1 of 2-amino-6-(methylisopropylamino)benzonitrile gives the title compound, m.p. 64°–67° C.

Analysis for: $C_{15}H_{19}N_3O_3$—Calculated: C, 62.26; H, 6.62; N, 14.52. Found: C, 62.30; H, 6.65; N, 14.53.

2-amino-6-(methylisopropylamino)benzonitrile is obtained by iron reduction as in Example 1.

2-(methylisopropylamino)-6-nitrobenzonitrile is obtained by the usual substitution using methylisopropylamine, m.p. 70°–72° C.

Analysis for: $C_{11}H_{13}N_3O_2$—Calculated: C, 60.26; H, 5.98; N, 19.15. Found: C, 60.21; H, 5.93; N, 19.19.

EXAMPLE 11

[2-Cyano-3-(Pyrrolidinyl)Phenylamino]Oxoacetic Acid Ethyl Ester

Oxalation of 2-amino-6-pyrrolidinylbenzonitrile as in Example 1 gives the title compound, m.p. 138°–141° C.

Analysis for: $C_{15}H_{17}N_3O_3$—Calculated: C, 62.70; H, 5.96; N, 14.63. Found: C, 62.81; H, 5.98; N, 14.61.

2-amino-6-pyrrolidinylbenzonitrile is prepared by iron reduction of the corresponding nitro derivative as in Example 1, m.p. 112°-114° C.

Analysis for: $C_{11}H_{13}N_3$—Calculated: C, 70.56; H, 7.00; N, 22.44. Found: C, 70.51; H, 6.71; N, 22.50.

2-nitro-6-pyrrolidinylbenzonitrile is prepared by the usual displacement (Example 6) using pyrrolidine, m.p. 111°-113° C.

Analysis for: $C_{11}H_{11}N_3O_2$—Calculated: C, 60.82; H, 5.10; N, 19.35. Found: C, 61.04; H, 5.14; N, 19.59.

EXAMPLE 12

[2-Cyano-3-(Morpholinyl)Phenylamino]Oxoacetic Acid Ethyl Ester

This is prepared from 2-amino-6-norpholinylbenzonitrile and ethyloxalyl chloride in the usual manner, m.p. 115°-117° C.

Analysis for: $C_{15}H_{17}N_3O_4$—Calculated: C, 59.39; H, 5.65; N, 13.86. Found: C, 59.21; H, 4.76; N, 13.69.

2-amino-6-morpholinylbenzonitrile is prepared by reduction of 2-(4-morpholinyl)-6-nitrobenzonitrile as in Example 1, m.p. 157°-160° C.

Analysis for: $C_{11}H_{13}N_3O$—Calculated: C, 65.00; H, 6.45; N, 20.68. Found: C, 64.81; H, 6.35; N, 20.79.

2-(4-morpholinyl)-6-nitrobenzonitrile is prepared by displacement with morpholine as in Example 6, m.p. 152°-155° C.

Analysis for: $C_{11}H_{11}N_3O_3$—Calculated: C, 56.65; H, 4.76; N, 18.02. Found: C, 56.95; H, 4.82; N, 18.35.

EXAMPLE 13

[2-Cyano-3-(4-Morpholinyl)Phenylamino]Oxoacetic Acid 1-Methylpropyl Ester

This material is prepared as in Example 12 using sec-butyloxalyl chloride instead of ethyl oxalyl chloride, m.p. 108°-111° C.

Analysis for: $C_{17}H_{21}N_3O_4$—Calculated: C, 61.62; H, 6.39; N, 12.68. Found: C, 61.42; H, 6.71; N, 12.95.

The following sodium salts are all prepared by the same procedure:

The oxoacetic acid ethyl ester is dissolved in ethanol at reflux exactly one equivalent of 5.9 N sodium hydroxide is added and the solution is allowed to cool. The resulting solid is filtered, washed with ethanol and dried to give the sodium salt.

EXAMPLE 14

[2-Cyano-3-(Methylamino)phenylamino]Oxoacetic Acid Sodium Salt, 2/5 hydrate, 1/5 Ethanolate m.p. 272°-275° C.(dec).

Analysis for: $C_{10}H_8N_3O_3 \cdot 1/5$ EtoH . 2.5 $H_2O$—Calculated: C, 48.49; H, 3.91; N, 16.31. Found: C, 48.70; H, 3.82; N, 16.29.

EXAMPLE 15

[2-Cyano-3-(Ethylmethylamino)Phenylamino]Oxoacetic Acid, Sodium Salt, 7/10 Hydrate m.p. 90°-94° C.

Analysis for: $C_{12}H_{12}N_3O_5Na \cdot 7/10$ $H_2O$—Calculated: C, 51.14; H, 4.79; N, 14.91. Found: C, 51.01; H, 4.65; N, 14.99.

EXAMPLE 16

[3-(Butylamino)-2-Cyanophenylamino]Oxoacetic Acid, Sodium Salt m.p. 252°-254° C.

Analysis for: $C_{13}H_4N_3O_3Na$—Calculated: C, 55.12; H, 4.98; N, 14.83. Found: C, 54.82; H, 4.80; N, 14.59.

EXAMPLE 17

[2-Cyano-3-(4-Morpholinyl)Phenylamino]Oxoacetic Acid, Sodium Salt, 4/10 Hydrate m.p. 170° C. (shrink), 240° C. (dec.).

Analysis for: $C_{13}H_{12}N_3O_4Na \cdot 4/10$ $H_2O$—Calculated: C, 51.28; H, 4.24; N, 13.80. Found: C, 51.35; H, 4.28; N, 13.91.

EXAMPLE 18

(4-Amino-2-Cyanophenylamino)Oxoacetic Acid Ethyl Ester 5.0 g. of (2-cyano-4-nitrophenylamino)oxoacetic acid ethyl ester in 150 ml. of ethanol and 0.4 g. of 10% Pd/C is hydrogenated until hydrogen uptake ceases. The reaction mixture is filtered through Celite ®, evaporated to dryness and the solid is recrystallized from ethanol, 4.1 g., m.p. 137°-139° C.

Analysis for: $C_{11}H_{11}N_3O_3$—Calculated: C, 56.65; H, 4.76; N, 18.02. Found: C, 56.49; H, 4.94; N, 18.09.

(2-cyano-4-nitrophenyl)oxoacetic acid ethyl ester is prepared by the usual ethyl oxalation of 2-amino-5 nitrobenzonitrile as in Example 1, m.p. 137°-319° C.

Analysis for: $C_{11}H_9N_3O_5$—Calculated: C, 50.19; H, 3.45; N, 15.97. Found: C, 49.99; H, 3.55; N, 15.98.

The oxalyl chloride ester employed in the synthesis of the compounds of this invention is preferable the ethyl ester, the sec-butyl ester or the cyclohexyl ester. However, other simple esters are similarly applicable, producing the corresponding ester products with unchanged biological activity, although assimilation by the host may vary somewhat. Thus, the esters initially produced may be lower alkyl (e.g. methyl, ethyl, propyl, i-propyl, butyl, sec-butyl, amyl, sec-amyl, hexyl, etc.); aralkyl (e.g. benzyl, Phenethyl, etc.); or cycloalkyl (e.g. cyclopentyl, cyclohexyl, etc.). Thus, the esters produced as part of this invention embrace esters in which the hydrocarbon moiety of the alcohol is alkyl of 1 to 5 carbon atoms, hydrocarbonic aralkyl of 7 or 8 carbon atoms or cycloalkyl of 5 or 6 carbon atoms.

What is claimed is:

1. A compound of the formula:

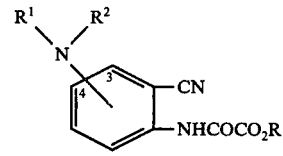

in which

R is —H; an alkali metal; $^+NH_4$; alkyl of 1 to 6 carbon atoms, inclusive; benzyl or phenethyl; or cycloalkyl of 5 or 6 carbon atoms; and $R^1$ and $R^2$ together, with the nitrogen atom to which they are attached, are aziridinyl, azetidinyl, pyrrolidinyl, piperidinyl, piperazinyl, 4-lower alkylpiperazinyl, morpholino or thiomorpholino;

or a pharmaceutically acceptable acid addition salt thereof.

2. A compound of claim 1 in which the group

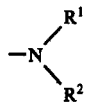

is in 3-position.

3. The compound of claim 1 which is 2-cyano-3-(1-piperidinyl)oxanilic acid, an alkali metal salt, the ammonium salt, or an alkyl ester containing from 1 to 6 carbon atoms in the alkoxy moiety.

4. The compound of claim 1 which is 2-cyano-3-(4-methyl-1-piperazinyl)oxanilic acid, an alkali metal salt, the ammonium salt, or an alkyl ester containing from 1 to 6 carbon atoms in the alkoxy moiety.

5. The compound of claim 1 which is [2-cyano-3-(pyrrolidinyl)phenylamino]oxoacetic acid, an alkali metal salt, the ammonium salt, or an alkyl ester containing from 1 to 6 carbon atoms in the alkoxy moiety.

6. The compound of claim 1 which is [2-cyano-3-(morpholinyl)phenylamino]oxoacetic acid, an alkali metal salt, the ammonium salt, or an alkyl ester containing from 1 to 6 carbon atoms in the alkoxy moiety.

* * * * *